United States Patent [19]

Shmulewitz et al.

[11] Patent Number: 5,660,185
[45] Date of Patent: Aug. 26, 1997

[54] IMAGE-GUIDED BIOPSY APPARATUS WITH ENHANCED IMAGING AND METHODS

[75] Inventors: Ascher Shmulewitz; Edo Ziring, both of Mercer Island, Wash.

[73] Assignee: NeoVision Corporation, Seattle, Wash.

[21] Appl. No.: 421,381

[22] Filed: Apr. 13, 1995

[51] Int. Cl.$^6$ .................................................. A61B 10/00
[52] U.S. Cl. ...................................... 128/749; 128/660.01
[58] Field of Search ................................ 128/653.1, 653, 128/754, 662.05, 662.06, 662.01, 654, 749; 378/20

[56] References Cited

U.S. PATENT DOCUMENTS

| | | | |
|---|---|---|---|
| 3,765,403 | 10/1973 | Brenden | 128/2 V |
| 3,963,933 | 6/1976 | Henkes, Jr. | 250/456 |
| 3,971,950 | 7/1976 | Evans et al. | 250/451 |
| 4,058,114 | 11/1977 | Soldner | 128/662.05 |
| 4,433,690 | 2/1984 | Green et al. | 128/660 |
| 4,434,799 | 3/1984 | Taenzer | 128/660 |
| 4,485,819 | 12/1984 | Igl | 128/660 |
| 4,599,738 | 7/1986 | Panetta et al. | 378/37 |
| 4,625,555 | 12/1986 | Fujii | 73/597 |
| 4,821,727 | 4/1989 | Leven et al. | 128/653 |
| 4,862,893 | 9/1989 | Martinelli | 128/662.03 |
| 4,875,478 | 10/1989 | Chen | 378/20 |
| 4,966,152 | 10/1990 | Gang et al. | 128/661.07 |
| 5,007,428 | 4/1991 | Watmough | 128/660.04 |
| 5,078,142 | 1/1992 | Sigzer et al. | 128/653.1 |
| 5,113,420 | 5/1992 | Davis, Jr. et al. | 378/20 |
| 5,158,088 | 10/1992 | Nelson et al. | 128/662.05 |

FOREIGN PATENT DOCUMENTS

| | | |
|---|---|---|
| 0 105 812 | 4/1984 | European Pat. Off. . |
| 32 22 053 | 12/1983 | Germany . |
| 32 27 624 | 1/1984 | Germany . |
| 34 05 537 | 8/1985 | Germany . |
| 40 37 387 | 5/1992 | Germany . |
| WO83/02053 | 6/1983 | WIPO . |

OTHER PUBLICATIONS

S.H. Parker et al., "Percutaneous Large–Core Breast Biopsy: A Multi–institutional Study," *Radiology*, Nov. 1994, pp. 359–364.

S.H. Parker et al., "US–guided Automated Large–Core Breast Biopsy", *Radiology*, May 1993, pp. 507–511.

E. Rubin, "Breast Cancer in the 90's", *Applied Radiology*, Mar. 1993, pp. 23–26.

G. Newstead, "When and when not to biopsy the breast", *Diagnostic Imaging*, Mar. 1993, pp. 11–116.

R.F. Brem and O.M.B. Gatewood, "Template–guided Breast US", *Radiology*, Sep. 1992, pp. 872–874.

B.D. Fornage et al., "Ultrasound–Guided Needle Biopsy Of The Breast And Other Interventional Procedures," *Radiologic Clinics Of North America*, vol. 30, No. 1, Jan. 1992, pp. 167–185.

W.F. Conway et al., "Occult Breast Masses: Use of a Mammographic Localizing Grid for US Evaluation", *Radiology*, Oct. 1991, pp. 143–146.

E.B. Mendelson, "Ultrasound secures place in breast Ca management", *Diagnostic Imaging*, Apr. 1991, pp. 120–129.

(List continued on next page.)

*Primary Examiner*—Sam Rimell
*Assistant Examiner*—Pamela L. Wingood
*Attorney, Agent, or Firm*—Fish & Neave; Nicola A. Pisano

[57] ABSTRACT

Apparatus and methods are provided for positioning a biopsy needle for insertion into a tissue mass by correlating, in real-time, the actual needle position prior to insertion with its probable trajectory once inserted. In a preferred embodiment, the biopsy needle location is tracked electronically and projected over a previously stored or real-time image of the tissue, thus allowing a clinician to observe which features of an imaged tissue the biopsy needle is likely to intersect upon insertion. Continued ultrasound scanning of a selected trajectory may be provided to assess depth of penetration of the biopsy needle, when inserted. Apparatus is also provided for expanding the region scanned by an ultrasound transducer beyond the periphery of a compression plate.

30 Claims, 7 Drawing Sheets

OTHER PUBLICATIONS

V.P. Jackson, "The Role of US in Breast Imaging", *Radiology*, Nov. 1990, pp. 303–311.

S.H. Parker and W.E. Jobe, "Large–core Breast Biopsy Offers Reliable Diagnosis," reprinted from *Diagnostic Imaging*, Oct. 1990.

F.M. Hall, "Mammographic Second Opinions Prior to Biopsy of Nonpalpable Breast Lesions", *Arch. Surg.*, Mar. 1990, pp. 298–299.

K. Dowlatshahi et al., "Nonpalpable Breast Tumors: Diagnostic with Stereotaxic Localization and Fine Needle Aspiration", *Radiology*, Feb. 1989, pp. 427–433.

B.D. Fornage et al., "Breast Masses: US–Guided Fine Needle Aspiration Biopsy", *Radiology*, Feb. 1987, pp. 409–414.

I. Andersson, "Mammography in Clinical Practice", *Medical Radiography and Photography*, vol. 62, No. 2, (1986) (Eastman Kodak Co.).

IMAGE-GUIDED BIOPSY APPARATUS WITH ENHANCED IMAGING AND METHODS

FIELD OF THE INVENTION

The present invention relates to apparatus and methods for performing biopsy of biological tissue, and more particularly, to performing biopsy of biological tissue guided by ultrasound imaging.

BACKGROUND OF THE INVENTION

Apparatus and methods are known to identify tumorous masses suspected of being malignant, for example, by radiographic and sonographic techniques. It is typical for such tissue masses to then be biopsied to determine status as, or degree of, malignancy, to determine further course of treatment. For example, a region of a mammogram suspected to contain a lesion may be biopsied to determine whether the lesion is benign or malignant, and if malignant, the course of treatment appropriate for the degree of malignancy, e.g. mastectomy, radiation treatment or chemotherapy.

Previously known biopsy methods range from minimally invasive techniques, such as fine needle aspiration using a 21 gauge hypodermic needle and large core biopsy using a 14 gauge needle mounted in an automated biopsy gun, to open-procedures in which the lesion is surgically excised. Minimally invasive techniques are faster, less expensive, safer and less traumatic for the patient than surgical excision, and begun developing widespread acceptance.

A concern common to previously known minimally invasive biopsy techniques, however, is ensuring that the biopsy needle actually obtains a tissue sample from the suspected lesion, rather than adjacent healthy tissue. Previously known techniques that attempt to ensure that the biopsy needle trajectory enters the region of the suspected lesion are described, for example, in Fornage et al., "Ultrasound-Guided Needle Biopsy Of The Breast And Other Interventional Procedures," Radiologic Clinics Of North America, Vol. 30, No. 1 (January 1992), Fornage et al. "Breast Masses: US-Guided Fine Needle Aspiration Biopsy," Radiology, 162:409–414 (February 1987), Parker et al., "US-guided Automated Large-Core Breast Biopsy," Radiology, 187:507–511 (May 1993), and Parker and Jobe, "Large-Core Breast Biopsy Offers Reliable Diagnosis," reprinted from Diagnostic Imaging (October 1990).

The foregoing articles describe a free-hand ultrasound technique, in which insertion of a biopsy needle into a suspected lesion is performed by holding a linear array ultrasound transducer in one hand and inserting the needle into the tissue with the other hand. In particular, the ultrasound transducer is held above the midline of the suspicious mass and the needle (or needle of the automated biopsy gun) is then inserted in the tissue near the base of the transducer, so that the tip of the needle appears in the ultrasound scan. In addition, when a biopsy gun is employed, additional personnel may be required to steady the biopsy gun during use or to hold the ultrasound transducer.

As described in the Fornage et al. articles and Parker et al. article, difficulties arise using the free-hand technique where the suspected lesion is located near the patient's chest wall, or in proximity to a prothesis. These articles also emphasize that the practitioner's level of skill in using the free-hand technique can dramatically influence the results obtained. All of the foregoing articles reject the use of biopsy needle guides that can be attached to the ultrasound transducer, because the guides interfere with the flexibility and maneuverability required to obtain satisfactory results.

The Parker and Jobe article also describes stereotactic mammographic biopsy systems. In such systems, two X-ray images of the breast tissue are made at different angles, thereby permitting the coordinates of a lesion to be calculated. The biopsy needle, typically an automated biopsy gun (e.g., Biopty from C. R. Bard, Inc., Bard Urological Division, Covington, Ga.) mounted in a rigid housing attached to the biopsy table, is moved to the calculated coordinates and actuated. Two additional X-ray views of the breast tissue are then taken to confirm that the needle has actually sampled the region of the suspected lesion.

The Parker and Jobe article further describes the drawbacks of add-on stereotactic systems—namely, the potential for breast movement that renders earlier stereo calculations worthless. That article also describes the Mammotest system sold by Fischer Imaging Corporation, Thornton, Colo., as overcoming some of the problems of add-on stereotactic systems, but at a considerable cost differential.

A drawback common to all of the stereotactic systems, however, is the need for multiple X-rays of the tissue, thus exposing the tissue to potentially unhealthful ionizing radiation. These systems also provide no real-time imaging of the needle trajectory, so as described in the Parker and Jobe article, intervening movement of the breast tissue may render the calculated coordinates useless and result in a potentially misleading biopsy sample. Indeed, the clinician is not even aware that the biopsy needle missed the intended target until after the follow-up stereotactic views are taken.

Moreover, because the biopsy needle is secured in a fixed housing so as to provide a fixed trajectory for biopsy needle, stereotactic systems provide no freedom of movement for the biopsy needle relative to the target tissue. Consequently, several needle insertions and withdrawals are required to adequately characterize the tissue.

A major disadvantage of the above-described previously known methods and apparatus arises due to the inability of the clinician to estimate, in real-time, the correct trajectory of the biopsy needle from the breast surface to the region of the suspected tumor or lesion. Even when guided by free-hand ultrasound scanning, the clinician typically must insert and withdraw the biopsy needle ten to fifteen times or more to improve the confidence level that a portion of the suspected lesion has been collected. Then, each of the needle aspiration samples must be separately tested, significantly increasing the overall cost of the procedure.

Likewise, in stereotactic systems, the inability to monitor tissue movement and to manipulate the biopsy needle once inserted, creates the need for multiple needle insertions to obtain adequate characterization of the suspected lesion. And again, each of these multiple samples must be individually tested to properly characterize the suspected lesion.

Such repetitive insertion and withdrawal of the biopsy needle may cause significant patient discomfort. Moreover, in those cases where the biopsy indicates no need for treatment by surgical methods, the repeated biopsy needle insertion may nevertheless leave the patient with cosmetically unappealing scar tissue.

A further disadvantage of these previously known methods and apparatus is the potential for seeding the needle tracks with potentially malignant tumor cells. For example, because the clinician in previously known methods must make several needle insertions to confirm that he or she has sampled cells from the target tissue, there is the potential that malignant cells may be dispersed along a needle track which was not believed by the clinician to have entered the region of the suspected tumor, but which in fact did so.

In view of the foregoing, it would be desirable to provide apparatus and methods by which a biopsy needle could be positioned for insertion so as to have a real-time, predetermined trajectory to a targeted tissue region, thereby reducing the need for repetitive needle insertion and withdrawal to obtain a biopsy sample.

It would also be desirable to provide apparatus and methods by which a biopsy needle could be positioned for insertion in real-time with a high degree of confidence that the needle trajectory will enter a targeted tissue region, thus reducing the risk of spreading potential malignant tumor cells by dispersing them along multiple needle tracks.

It would also be desirable to provide apparatus and methods by which a biopsy needle could be positioned for insertion into tissue along a predetermined trajectory, and which enables the clinician to alter that trajectory once the needle has been inserted, so as to reduce the number of scars resulting from repetitive skin punctures.

A yet further drawback of previously known biopsy systems, including those employing ultrasonic imaging of the biological tissue, is the inability to assess tissue features located near, or extending within, the chest wall. Such features typically have been inaccessible to previously known radiographic and sonographic imaging techniques due to the inability, for example, to direct such X-radiation to the X-ray film, while in sonographic systems, complicated structures including submersing the tissue in a water bath have been required.

It therefore would be desirable to provide a biopsy system having enhanced imaging capability to provide images of biological features located near or within a patient's chest line.

SUMMARY OF THE INVENTION

In view of the foregoing, it is an object of this invention to provide a apparatus and methods by which a biopsy needle may be initially positioned in real-time for insertion so as to have a predetermined trajectory to a targeted tissue region. In this manner, the need for repetitive needle insertion and withdrawal to obtain a biopsy sample is reduced, improving the efficiency of the medical procedure, and reducing patient distress during the medical procedure.

It is another object of this invention to provide apparatus and methods by which a biopsy needle may be positioned for insertion in real-time with a high degree of confidence that the needle trajectory will enter a targeted tissue region, thereby reducing the risk of spreading potential malignant tumor cells by dispersing them along multiple needle tracks.

It is yet another object of the present invention to provide apparatus and methods by which a biopsy needle may be positioned for insertion into tissue along a predetermined trajectory, and which enables the clinician to alter the needle trajectory once the needle has been inserted, thus reducing the number of scars resulting from repetitive skin punctures as well as patient discomfort.

It is yet a further object of this invention to provide apparatus and methods by which a clinician can image biological features within tissue that are located near, or extend within, a patient's chest wall, thereby enabling more thorough examination of the tissue and more thorough biopsy, if indicated.

These and other objects of the invention are accomplished in accordance with the principles of the invention by providing apparatus and methods in which a biopsy needle is guided to an initial insertion position by correlating, in real-time, the actual needle position prior to insertion with its probable trajectory once inserted. In a preferred embodiment, the needle location is tracked electronically and projected over a previously stored or real-time image of the tissue. The clinician may then observe which features of the imaged tissue the biopsy needle is likely to intersect when inserted. Additionally, ultrasound scanning of a selected trajectory may also be provided to assess depth of penetration of the biopsy needle, when inserted.

The ultrasound scanning provided by the apparatus of the present invention may include the capability, by angling either the ultrasound transducer or the upper compression plate relative to the chest wall, to provide imaging of biological features located near, or extending within, the chest line.

Further features of the invention, its nature and various advantages will be more apparent from the accompanying drawings and the following detailed description of the preferred embodiments.

DETAILED DESCRIPTION OF THE INVENTION

The present invention is directed to a system for performing biopsy of biological tissue, as indicated by, for example, a sonogram or mammogram. In overview, the apparatus of the present invention uses a previously stored or real-time ultrasound image to determine an initial position for a biopsy needle so that there is a high degree of confidence that the needle trajectory will intersect a target tissue region, for example, a suspected lesion.

In a first illustrative embodiment described herein, the biopsy system includes stand-alone sonography apparatus. In an alternative embodiment, the biopsy system may be used in conjunction with a sonomammography system as described in copending, commonly assigned patent application Ser. No. 08/277,894, filed Jul. 20, 1994, which is incorporated by reference herein in its entirety.

Figure 1:
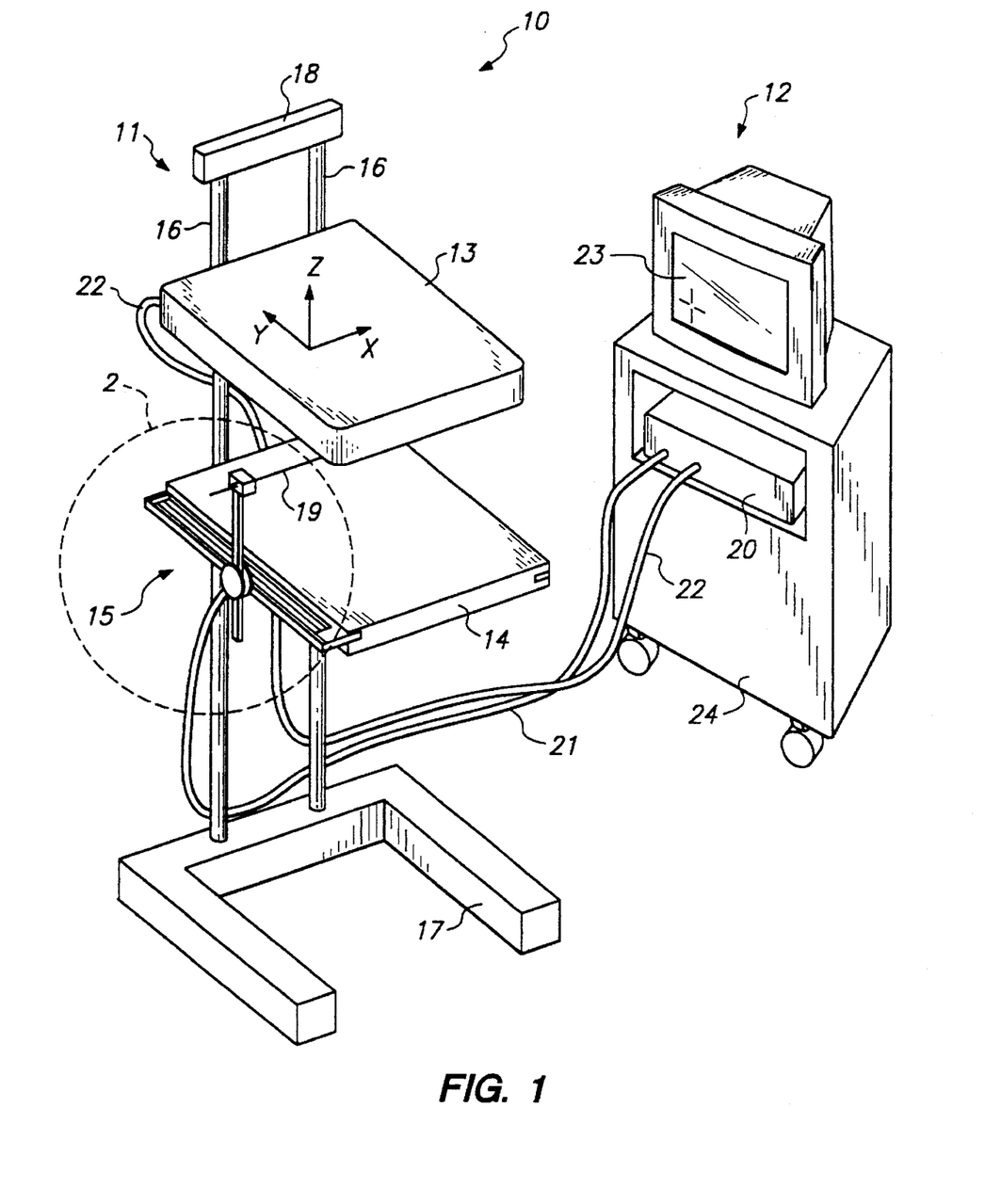
FIG. 1 is a perspective view of an illustrative embodiment of the biopsy system of the present invention.

Referring now to FIG. 1, biopsy system 10 constructed in accordance with the principles of the present invention is described. System 10 comprises biopsy table 11 and computer-based display system 12. Biopsy table 11 includes ultrasonic scanner 13, tissue support table 14, and needle support system 15 movably mounted on support members 16 between base 17 and top block 18. Biopsy needle 19 is releasably carried by needle support system 15, as described in detail hereinafter. Needle support system 15 is detachably coupled to computer 20 of computer-based display system 12 by cable 21, so that movement of biopsy needle is displayed by monitor 23 of computer-based display system 12.

Ultrasonic scanner 13 may be constructed as described with respect to FIG. 7 of the above-incorporated U.S. patent application Ser. No. 08/277,894, so as to include an annular or linear array ultrasonic transducer mounted for movement in an X-Y plane as indicated by the axes shown in FIG. 1 herein. In particular, the ultrasound transducer may be mounted on a carriage that is driven by a system of belts, cables, drive screws, or similar mechanisms to provide scanning along a series of planes sufficient to generate a three-dimensional data model of the tissue to be biopsied.

Ultrasonic scanner 13 includes a lower surface that functions as an upper compression plate, for immobilizing tissue against tissue support table 14. While the compression plate of ultrasonic scanner 13 may be constructed of any of the materials described in the above-incorporated application, it will of course be understood that radiolucency of the compression plate is not required for stand-alone sonographic applications of the present invention. Ultrasonic scanner 13 may also incorporate certain improvements, described in detail hereinafter, that enable imaging of biological features located near, or within, the patient's chest line. Imaging data generated by ultrasonic scanner is provided to computer-based display system 12 via cable 22.

Tissue support table 14 of the illustrative embodiment of FIG. 1 comprises a sturdy material, e.g., metal, fiberglass or plastic, such as UHMW plastic (e.g., ultra high molecular weight polyethylene), or combinations thereof, and serves to support the lower surface of the biological tissue in compression. In particular, tissue support table 14 and ultrasonic scanner 13 may be releasably and adjustably mounted to support members 16 to provide both adequate compression of the tissue and to provide height adjustment to accommodate the size of the patient.

Computer-based display system 12 is illustratively shown comprising monitor 23 and computer 20 disposed on movable cart 24. Computer 20 may be a general purpose personal computer, having for example, an 80386 or greater microprocessor, or similar processor, and a hard disk drive, or similar memory device sufficient for storing software programs, to manipulate imaging data generated by ultrasonic scanner 13 and positioning data generated by needle support system 15. As will of course be understood, system 12 includes one or more additional cards for processing data received from ultrasonic transducer 13 and needle support system 15, the implementation details of which employ routine application of ultrasound signal acquisition principles, and which therefore form no part of the present invention.

Figure 2:
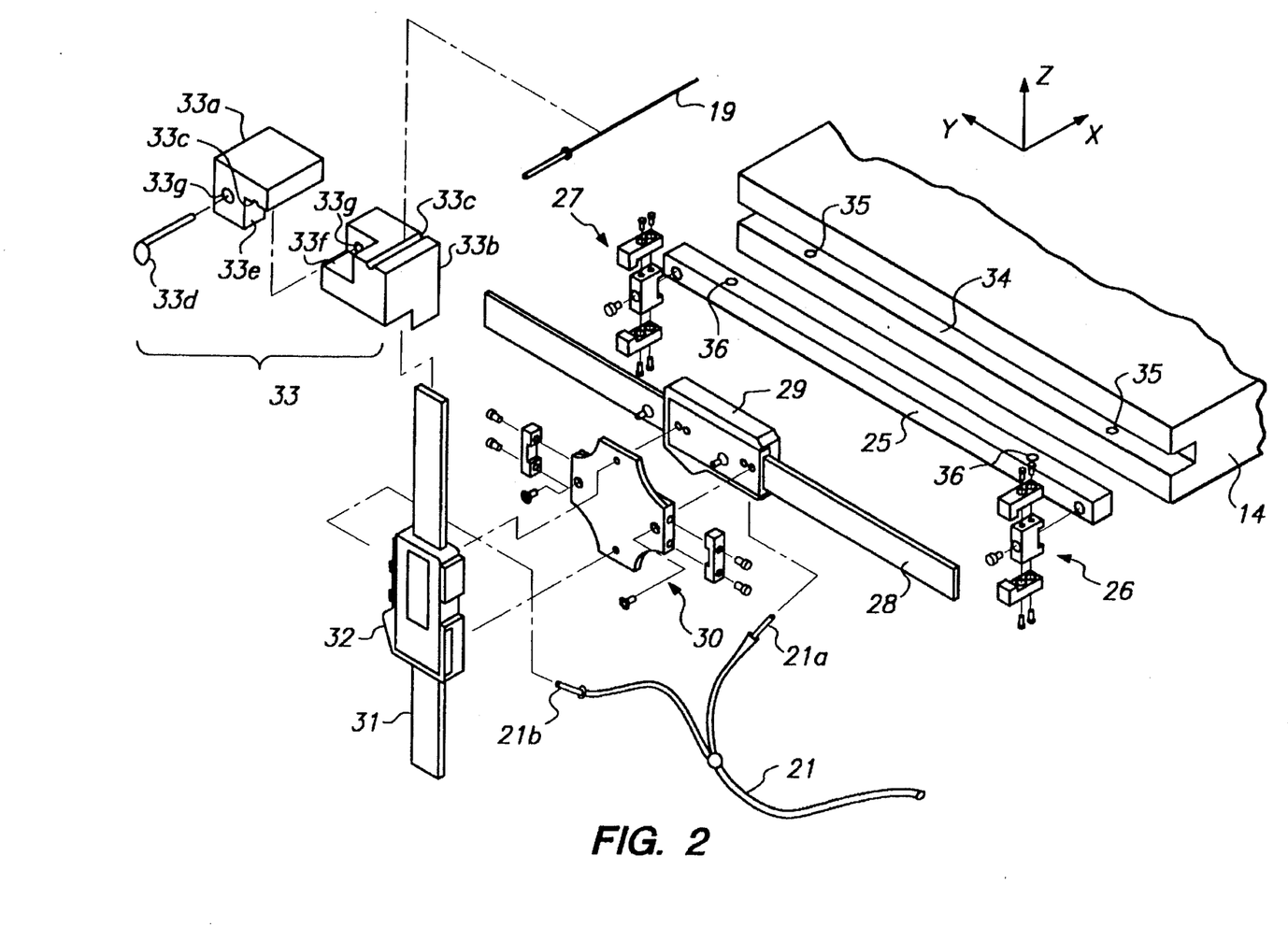
FIG. 2 is an exploded perspective enlarged view of a portion of the biopsy system of FIG. 1, indicated in inset 2 of FIG. 1.

Referring now to FIG. 2, an illustrative embodiment of needle support system 15 is described. Needle support system 15 includes anchor bar 25, support block assemblies 26 and 27, Y-axis track 28, Y-axis linear encoder 29, support plate assembly 30, Z-axis track 31, Z-axis linear encoder 32, and needle support block assembly 33.

Anchor block 25 is dimensioned to fit with close tolerances into grooves 34 provided in the lateral sides of tissue support table 14. Positioning holes 35 are provided in the grooved portion of tissue support table 14 so that locking pegs (not shown) can be extended through holes 35 and into holes 36 of anchor block 25, thus positively locking anchor block 25 (and thus needle support system 15) into known relation with tissue support table 14.

The combination of groove 34 and anchor block 25 provides a high degree of rigidity to the overall needle support system, while provision of grooves 34 on each side of tissue support table 14 enables the clinician to obtain access to the tissue from either the left or right side. In addition, ultrasonic scanner 13 and tissue support table 14 may be adjustably mounted, for example, to a block that is in turn pivotally connected to support members 16, so as to enable the entire biopsy system to be rotated relative to the biological tissue, thus offering additional areas of access to the tissue.

Support block assemblies 26 and 27 rigidly fasten Y-axis track 28 to anchor block 25, and thus tissue support table 14. Y-axis linear encoder 29 comprises, for example, an incremental binary counter, and is slidably movable along the length of Y-axis track 28. In a preferred embodiment, the Y-axis track has disposed within it a printed circuit board arrangement of parallel, spaced-apart copper strips, while Y-axis linear encoder 29 includes a head that senses the static capacitance of the copper strips as the encoder is manually slid along Y-axis track 28, and circuitry for interpolating between adjacent copper strips. As Y-axis linear encoder 29 is moved along track 28, it outputs a signal corresponding to its displacement from a preset reference point, preferably, a hard stop at a distal-most position from the patient's chest wall. The signal output by linear encoder 29 is provided to computer 20 via connecting cable 21, which connects to encoder 29 through jack 21a.

Support plate assembly 30 rigidly connects Z-axis linear encoder 32 to Y-axis linear encoder 29. Z-axis track 31 is slidably engaged in linear encoder 32, so that linear encoder 32 generates a signal corresponding to the displacement of Z-axis track relative to linear encoder 32 when track 32 is raised and lowered. The signal output by linear encoder 32 is provided to computer 20 via connecting cable 21, which connects to encoder 32 through jack 21b. Linear encoder 32 may use, for example, either the upper surface of tissue support table 14, or the lower surface of ultrasonic scanner 13, as its reference point. Linear encoders 29 and 32 preferably have a displacement accuracy of about plus/minus 0.05 mm, and can be reset via switches on encoders 29 and 32, or via software control.

Linear encoder 29 includes means, not shown, for locking the encoder in position along Y-axis track 28, while linear encoder 32 includes means (not shown) for locking Z-axis track 31 in position in encoder 32. Linear encoders 29 and 32, and mating tracks 28 and 31, are available from Sylvac S. A., Crissier, Switzerland, and distributed in the United States by Fowler Company, Inc., Chicago, Ill., as Part Nos. 54-050-035 (for Y-axis encoder 29) and 54-050-000 (for Z-axis encoder 32).

In addition, as will of course be understood by persons of skill in the art, linear encoders 29 and 32 may also comprise suitably designed rotary encoders, for example, as are used in computer mice and videogame joysticks, or other suitable displacement sensing components, such as linear variable displacement transducers or linear potentiometers.

Needle support assembly 33 comprises a biopsy needle holder that holds the biopsy needle securely during initial positioning and insertion, but detachably releases biopsy needle to allow free-hand movement of the biopsy needle once it has been inserted into a patient's tissue.

In the illustrative embodiment of FIG. 2, needle support assembly includes upper block 33a and lower block 33b. Needle support member is detachably coupled to the upper end of Z-axis track 31, for example, by a slot (not shown) in the lower surface of lower block 33b. Upper block 33a includes semi-circular channel 33c in its lower surface while lower block 33b includes semi-circular channel 33c in its upper surface. The channels in upper block 33a and lower block 33b mate when the two pieces are positioned together, thus forming a bore through which biopsy needle 19 may be slidably disposed.

Upper block 33a and lower block 33b preferably also have mating projections and concavities, for example, in the illustrative embodiment of FIG. 2, block-like projection 33e and corresponding indentation 33f. Bore 33g aligns across upper block 33a and lower block 33b when the two blocks are mated together, to permit pin 33d to be slidably disposed in bore 33g. In this manner, upper block 33a and lower block 33b may be rigidly fastened together by pin 33d to carry biopsy needle 19 during initial positioning and insertion of biopsy needle 19. When inserted in the bore formed by channels 33c, the biopsy needle has a trajectory aligned with the bore.

Once the needle is inserted in the patient, pin 33d may be removed from bore 33g, permitting removal of upper block 33a and movement of lower block 33b out of the clinician's way. This arrangement permits the clinician to thus remove the biopsy needle from needle support assembly 33 and manipulate it manually, while observing movement of the needle tip via display 23. Accordingly, needle support assembly 33 permits the biopsy needle to be initially positioned with the accuracy of a stereotactic biopsy system, while providing the flexibility and maneuverability of free-hand ultrasound techniques.

Figure 3A:
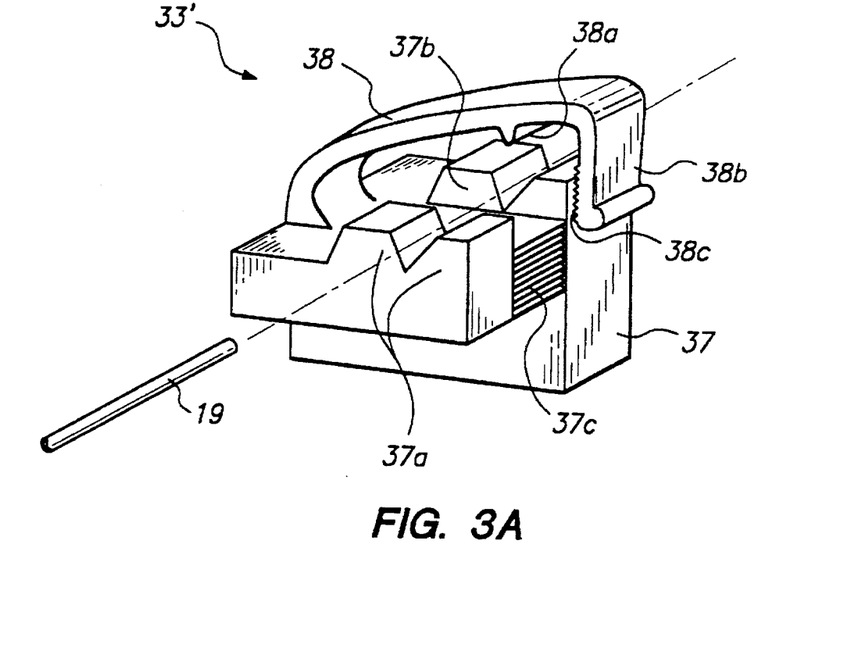
FIGS. 3A–3C are perspective and elevational views, respectively, of an alternative needle support assembly in the open and closed positions.
Figure 3B:
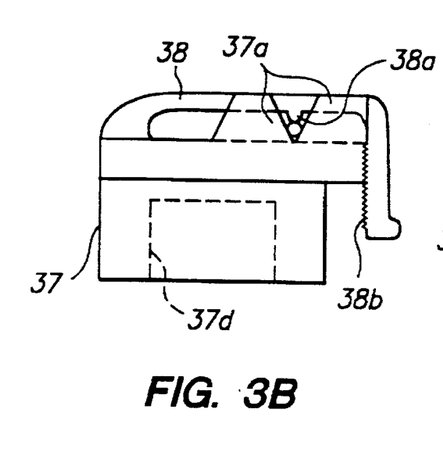

An alternative illustrative embodiment of needle support assembly 33' is described with respect to FIGS. 3A–3B. As shown in FIG. 3A, needle support assembly 33' comprises a block 37 having a V-shaped channel formed in elements 37a and 37b, and integrally formed locking arm 38. Locking arm 38 includes ridge 38a disposed to engage biopsy needle 19 when in a closed position. Locking arm also includes latch portion 38 including serrations 38c that interengage serrations 37c on block 37.

Figure 3C:
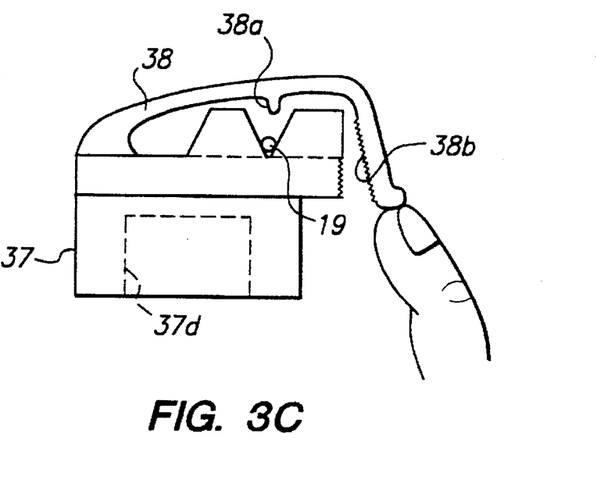

Locking arm 38 is dimensioned so that it fits with close tolerances between elements 37a and 37b, thereby enabling ridge 38a to engage biopsy needles having a wide range of diameters. As illustrated in FIGS. 3B and 3C, needle support block 33' may include slot 37d disposed therein for coupling the support to Z-axis track 31. Locking arm 38 securely engages biopsy needle 19 within the V-shaped channel formed in elements 37a and 37b for image-guided positioning of biopsy needle 19 relative to the patient's tissue, but permits the biopsy needle to be readily released from needle support assembly 33' by lifting locking arm 38 up and away from block 37.

Needle support assemblies 33 and 33' are preferably comprised of sturdy, lightweight materials that are capable of being sterilized. For example, needle support assemblies 33 and 33' may comprise machined aluminum that can be repeatedly sterilized, or injection-molded plastic elements that are disposed of after a single use. Needle support assembly 33' is preferably integrally molded from a suitable plastic, such as, polyethylene.

Figure 4:
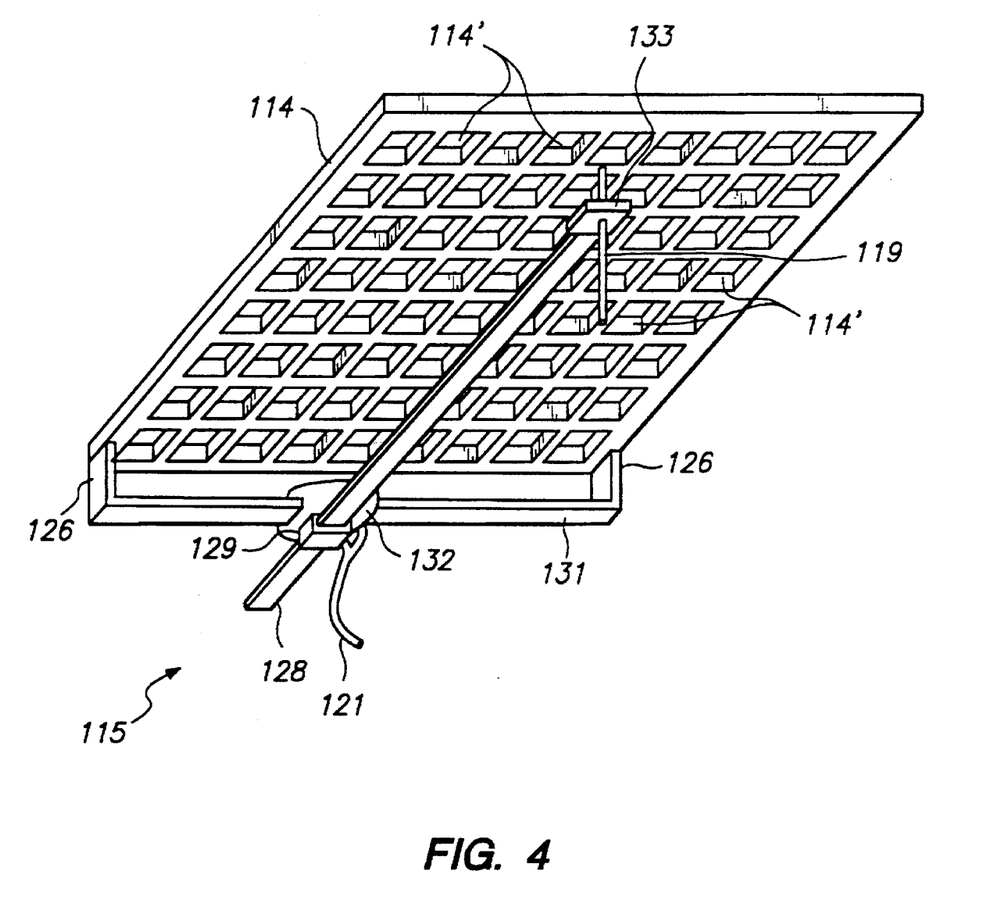
FIG. 4 is a perspective view from beneath of an alternative arrangement of the biopsy system of FIGS. 1 and 2.

Referring now to FIG. 4, an alternative embodiment of the biopsy system of FIGS. 1–3 is described, in which elements similar to those of the system of FIGS. 1–3 are indicated by reference numerals increased by 100, e.g., biopsy needle support system 115.

The biopsy system of FIG. 4 differs from that of FIGS. 1–3 in that tissue support table 114 comprises a grid-like structure having a multiplicity of apertures 114' and needle support system 115 is disposed beneath tissue support table 114. As will be apparent from FIG. 4, the arrangement of the system of FIG. 4 permits biopsy of the tissue to be performed through the lower surface of the breast, thus reducing the prominence of scarring associated with needle punctures. It is also to be understood that the multiplicity of apertures 114' extends over the entire area of tissue support table 114 used to support the patient's tissue (indicated in FIG. 4 by dots).

In preferred embodiment of the system of FIG. 4, tissue support table 114 has a thickness of about 0.5 inch (12.7 mm) and is formed of a suitable rigid plastic, metal alloy, or combination thereof. Tissue support table 114 includes a multiplicity of square apertures about 1.5 inches (38 mm) on a side, at a spacing sufficient to enable access to most of the underside of the patient's tissue with a minimum of repositioning.

With reference to the directional axes shown in FIGS. 1 and 2, needle support system 115 of FIG. 4 lies in the X-Y plane, and comprises Y-axis track 128, Y-axis linear encoder 129, X-axis track 131, X-axis linear encoder 132, and needle support assembly 133. X-axis track 131 is mounted to tissue support table 114 by support block assemblies 126, with Y-axis linear encoder 132 slidably engaged thereon. Y-axis track 128 is slidably engaged in Y-axis linear encoder 129, which is in turn coupled to X-axis linear encoder as described above with respect to FIG. 2. Y-axis track 128 carries needle support assembly 133 that engages biopsy needle 119.

Needle support system 115 is connected to computer-based display system 12 via cable 121. Except for the different physical arrangement of the components of the system of FIG. 4 as just described, the description provided hereinabove with respect to the system of FIGS. 1–3 otherwise applies to the system of FIG. 4.

Figure 5:
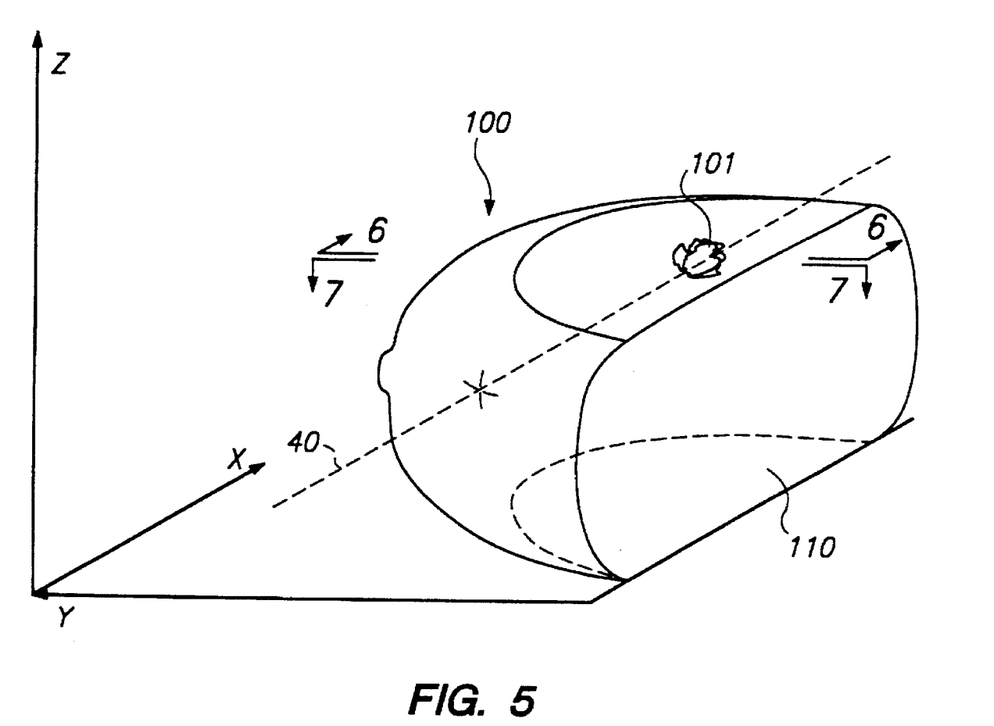
FIG. 5 is a perspective view of compressed breast tissue showing the reference axes employed with the biopsy system of the present invention.

Operation of the system of FIGS. 1–4 is now described with reference to FIGS. 5–7. Referring now to FIG. 5, a mass of biological tissue 100, specifically a human breast, is shown as it would appear when compressed between the upper surface of tissue support table 14 and the lower surface of ultrasonic scanner 13 (for clarity, ultrasonic scanner 13 and tissue support table 14 are not depicted in FIG. 5). It will of course be understood that tissue 100 remains connected to the patient. Tissue 100 contains within it region 101 corresponding to a suspected lesion.

FIG. 5 illustrates the reference axes referred in the following description. In particular, the Y-axis is the direction extending perpendicularly from the patient's chest wall (plane 110), the z-axis direction is elevational, and the x-axis direction extends in a parallel manner along the patient's chest wall. Projected needle trajectory 40 contacts the skin of tissue 100 at location 41 and intersects region 101 of the suspected lesion.

In operation, a patient's tissue mass is compressed between a lower compression surface of ultrasonic scanner 13 and the upper surface of tissue support table 14, thereby taking on the shape of tissue mass 100 of FIG. 5. A gel pad may be used to distribute the compressive loading over the tissue mass, to ease the patient's discomfort, and to improve coupling of the ultrasonic scanner to the tissue mass.

The clinician may then conduct a thorough ultrasound examination of the tissue by operating ultrasonic scanner 13 to generate a series of two-dimensional slices in the Y-Z or X-Z planes. These slices may then be digitally manipulated to provide a holographic image on display 23 of the interior features of the tissue mass, or to provide a view of any desired plane through the tissue.

When a biopsy is indicated, the clinician couples a fresh needle support assembly 33 or 33' to Z-axis track 31 and engages the biopsy needle with the needle support assembly. The clinician then selects a viewplane for viewing on display 23, such as an elevation view (i.e., in the Y-Z plane) through tissue 100, as shown in FIG. 6. As the biopsy needle is manually moved by the clinician in the Y-Z plane adjacent to tissue 100, encoders 29 and 32 of needle support system 15 output a signal that is processed by computer 20 and projected on the ultrasound image of the selected viewplane as, for example, cross-hair 45. It will of course be understood that the dimensions of needle support assembly are well controlled so that parallax between the location of the biopsy needle and the location of encoders 29 and 32 is properly taken into account.

Figure 6:
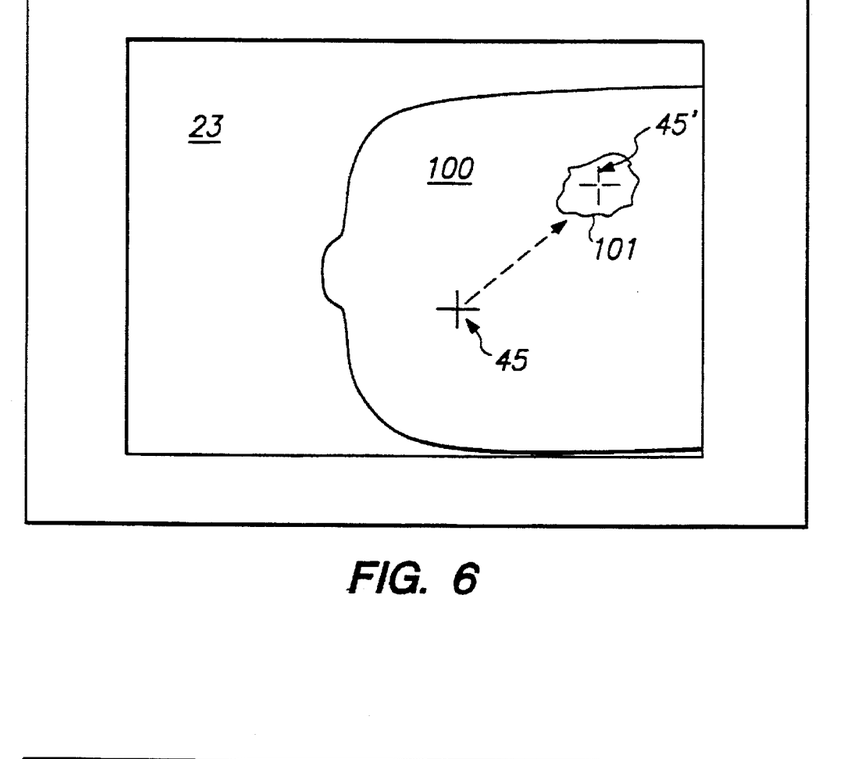
FIG. 6 is an illustrative Y-Z display of the compressed breast tissue of FIG. 5, taken along line 6—6 of FIG. 5.
Figure 7:
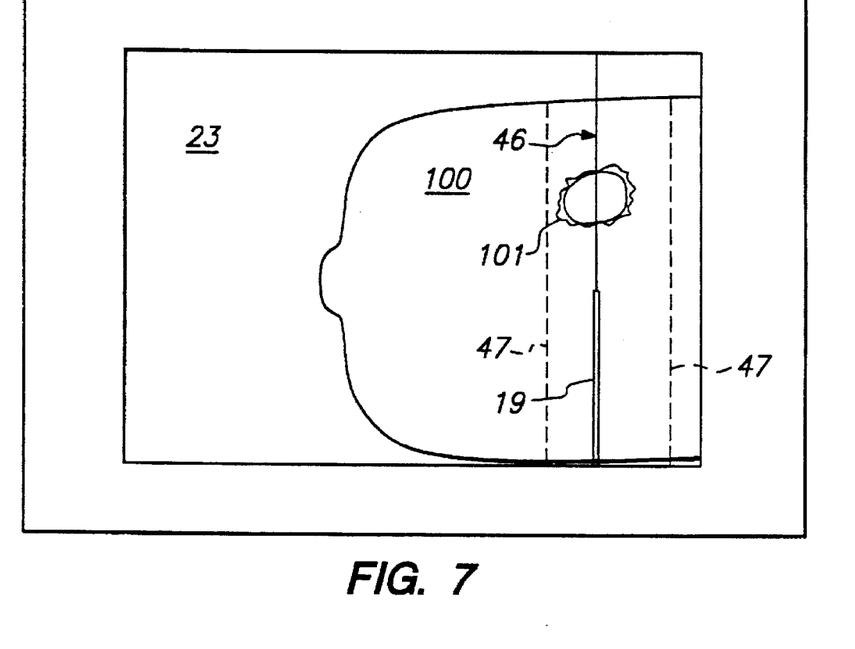
FIG. 7 is an illustrative X-Y display of the compressed breast tissue of FIG. 5, taken along line 7—7 of FIG. 5, showing a biopsy needle partially inserted into the tissue.

By manually moving biopsy needle 19 adjacent to tissue 100, needle support system 15 provides computer 20 with corresponding coordinates that enable the clinician to align cross-hair 45 with region 101 of the suspected lesion (shown in FIG. 6 by dotted arrow moving cross hair 45 to dotted cross-hair 45').

Once cross-hair 45 is aligned with region 101, the clinician may select additional views through tissue 100 to assess the trajectory of the biopsy needle. For example, the clinician may choose a plan view (i.e., in the X-Z plane) through tissue 100, as shown in FIG. 7, to indicate the trajectory of biopsy needle 19. In a plan view such as that of FIG. 7, the biopsy needle is preferably projected onto the ultrasound image as line 46, rather than a cross-hair.

Biopsy system 10 further provides for continually updating the ultrasound image of the entire tissue mass 100, or of a selected portion thereof, by operating ultrasonic scanner 13 to continually generate images of the tissue interior. Thus, for example, when the clinician has aligned the biopsy needle with region 101, he or she may lock needle support system 15 against further movement in the Y-Z plane, and issue appropriate commands to the ultrasonic scanner to scan only that portion of tissue 100 in the vicinity of the biopsy needle trajectory, for example, within dotted lines 47 shown in FIG. 7.

The clinician then extends biopsy needle 19 into tissue 100 by sliding the needle in the X-direction through the needle support assembly to enter the patient's tissue. If the plan view of the ultrasound image is displayed, as shown in FIG. 7, the clinician may then monitor the progress of the biopsy needle as it penetrates the tissue mass.

After the clinician has obtained a sample of region 101 along line 46 of the trajectory of biopsy needle 19, he or she may then remove pin 33d to release biopsy needle 19 from needle support assembly 33 or locking arm 38 of needle support assembly 33'. The clinician may then manipulate the biopsy needle to collect additional samples of region 101 under ultrasound image guidance, without having to create additional puncture wounds in the skin of tissue 100.

Operation of the system of FIG. 4 is similar to that described above, except that needle support system 115 is manipulated in an X-Y plane located beneath the patient's breast. Once the clinician has obtained a complete ultrasound image of the interior features of the tissue 100, a view in the X-Y plane is selected, which view would appear similar to that of FIG. 6. As needle support system 115 is manipulated, corresponding cross-hair 45 moves about on the displayed ultrasound view plane, as depicted in FIG. 6.

Biopsy needle may then be inserted through the nearest aperture 114' in tissue support table 114 to perform the biopsy. Similar to the system of FIGS. 1–3, progression of the biopsy needle as it is inserted in tissue 100 can be obtained by subsequent imaging using ultrasonic scanner 13. In particular, images generated in the Y-Z plane using the system of FIG. 4 will have an appearance similar to that of shown in FIG. 7.

As described above, biopsy system 10 of the present invention provides significant benefits over previously known systems and techniques. Unlike free-hand ultrasound techniques, the present invention provides precise initial positioning of the biopsy needle, so that the clinician has a high degree of confidence that the proposed trajectory of the biopsy needle will intersect the region of interest, thus reducing the number of needle insertions/withdrawals and the risk of seeding malignant cells along multiple needle tracks.

Moreover, the present invention provides continuous monitoring of the biopsy needle over the entire extent of the needle track, as opposed free-hand techniques that display only the portion of the needle that comes within the ultrasound scan. For example, free-hand ultrasound techniques provide no information about the biopsy needle trajectory until the needle has already punctured the skin; by contrast, the present invention enables prediction of the needle trajectory before it is even inserted.

Biopsy system 10 of the present invention likewise provides significant advantages over stereotactic X-ray systems. For example, the biopsy system of the present invention eliminates the use of hazardous ionizing radiation attendant with use of X-rays, eliminates the need for calculating coordinates for needle placement, provides real-time monitoring of the actual needle trajectory without the need for follow-up imaging, and enables the clinician to sample multiple areas within a target region through a single puncture wound. Moreover, the system of the present invention is less complex than stereotactic X-ray systems, and proportionately less expensive to build, use and maintain.

It will further be understood that the biopsy system of the present invention may be used with other ultrasonic scanning apparatus, for example, in conjunction with the sonomammography apparatus described in the above-incorporated U.S. patent application. For example, to use the biopsy system 15 of the present invention in an X-ray system including an ultrasonic scanner as described in the aforementioned application, needle support system 15 may be anchored to a dummy X-ray film cassette. The dummy X-ray film cassette is installed in the film holder/diffraction grid assembly of the X-ray system (often called a "Bucky"), to permit combined use of the ultrasonic scanner and biopsy needle support system as described hereinabove.

Figure 8:
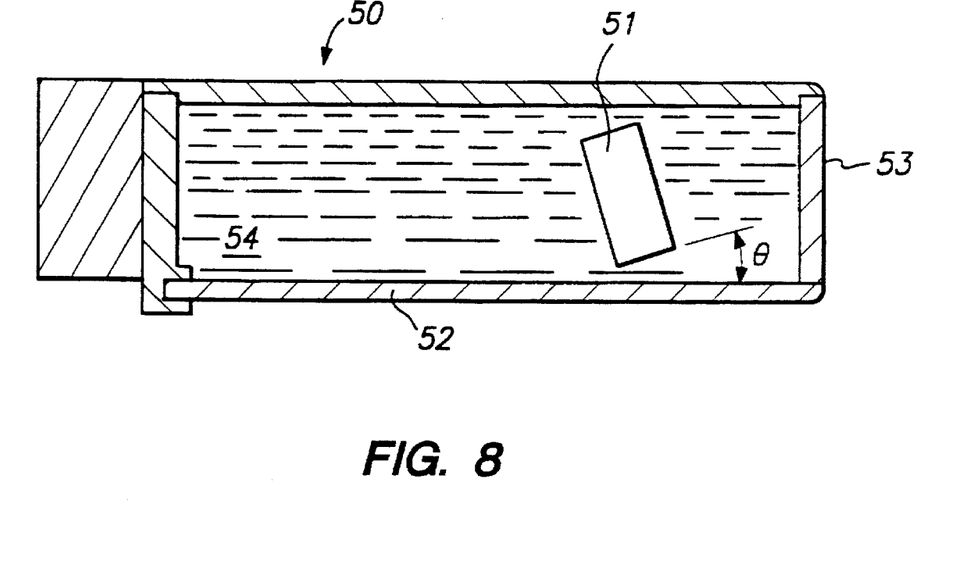
FIG. 8 is a cross-sectional view of an ultrasound scanning system constructed in accordance with the present invention that enables imaging of biological features located near, or extending within, the patient's chest line.
Figure 9:
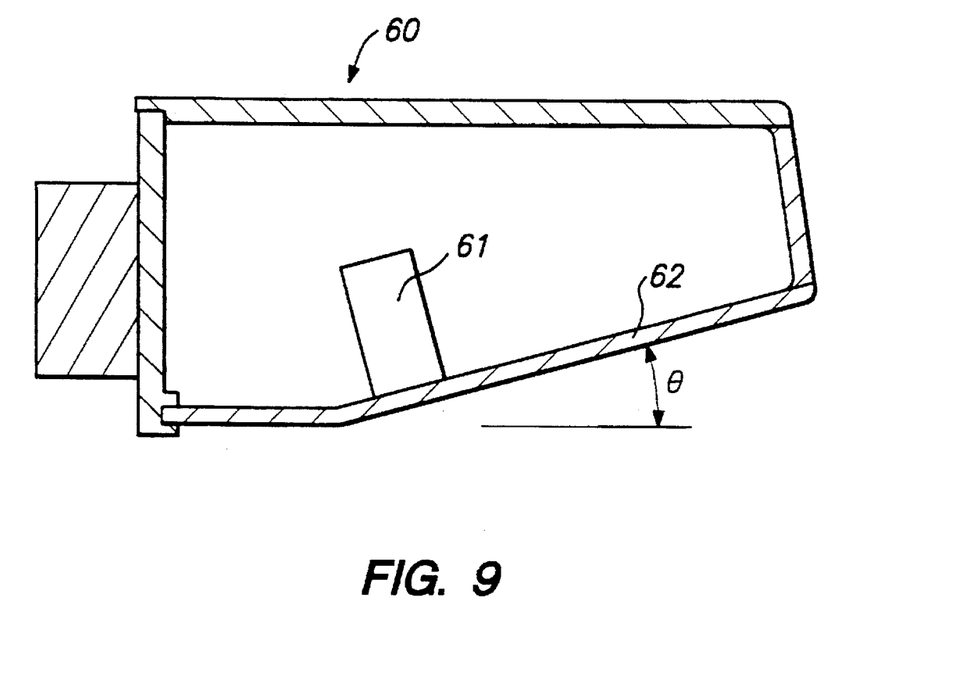
FIG. 9 is a cross-sectional view of an alternative embodiment of the system of FIG. 8.

Referring now to FIGS. 8 and 9, further features are described which are suitable for use in the biopsy system of the present invention. Referring to FIG. 8, a cross-section of ultrasonic scanner 50 is shown which is essentially similar in design to the ultrasonic scanner 13 described above and in the above-incorporated U.S. patent application Ser. No. 07/277,894. Ultrasonic scanner 50 differs from the above-described embodiments in that transducer 51 is not coupled to compression plate 52 directly, but is instead canted at an angle Θ away from the compression plate. In addition, both compression plate 52 and front panel 53 are constructed of a rigid sonolucent material.

Proper acoustic coupling between transducer 51 and compression plate 52 is obtained in ultrasonic scanner 50 by filling it with water 54 or another suitable acoustically transmissive medium. This arrangement is expected to enable ultrasonic scanner 50 to provide imaging not only of tissue disposed directly below the scanner, but also to provide imaging of tissue located near, or within, the patient's chest wall.

FIG. 9 provides an alternative embodiment of an ultrasonic scanner designed to provide enhanced imaging. In particular, ultrasonic scanner 60 of FIG. 9 is similar in design to ultrasonic scanner 13 described hereinabove, except that ultrasonic transducer 61 and compression plate 62 are canted at an angle Θ' to the horizontal. Since transducer 61 and compression plate 62 are both angled, transducer 61 may be acoustically coupled to compression plate 62 using coupling means described in the above-incorporated application. The inclined angle of compression plate 62 is also expected to enable ultrasonic imaging of internal features located near, or extending within, the patient's chest wall.

While preferred illustrative embodiments of the present invention are described above, it will be obvious to one skilled in the art that various changes and modifications may be made therein without departing from the invention and it is intended that the appended claims cover all such changes and modifications which fall within the true spirit and scope of the invention.

What is claimed is:

1. Apparatus for positioning a tip of a biopsy device for insertion into a selected region of a tissue mass, the apparatus for use in a system including display means, the apparatus comprising:

an ultrasonic scanner that provides an image of the tissue mass, the image of the tissue mass, including the selected region, displayed on the display means;

a support for holding a tip of a biopsy device with a trajectory;

means, other than the ultrasonic scanner, coupled to the support for generating a signal corresponding to a current location of the tip of the biopsy device, prior to insertion into the tissue mass, the signal being displayed on the display means by a symbol representative of the current location of the tip of the biopsy device relative to the selected region, wherein aligning the symbol with the selected region corresponds to moving the support to position at which the trajectory of the tip of the biopsy device will intersect the selected region.

2. The apparatus as defined in claim 1 wherein the support comprises first and second support tracks disposed in orthogonal relation to one another.

3. The apparatus as defined in claim 1 wherein the means for generating a signal comprises at least one encoder.

4. The apparatus as defined in claim 1 wherein the ultrasonic scanner provides real-time imaging of the tissue mass.

5. The apparatus as defined in claim 4 wherein the ultrasonic scanner provides imaging of the tip of the biopsy device after the tip of the biopsy device has been inserted into the tissue mass.

6. The apparatus as defined in claim 1 wherein the support releasably holds the biopsy device, so that the biopsy device may be released from the support after insertion of the tip of the biopsy device into the tissue mass to enable free-hand manipulation of the biopsy device.

7. The apparatus as defined in claim 1 wherein the ultrasonic scanner forms a first compression surface, the apparatus further comprising a tissue support table forming a second compression surface, the tissue mass immobilized between the first and second compression surfaces.

8. The apparatus as defined in claim 2 further comprising a tissue support table, the first support track removably anchored to the tissue support table.

9. The apparatus as defined in claim 2 further comprising a dummy X-ray film cassette, the first support track anchored to the dummy X-ray film cassette.

10. The apparatus as defined in claim 1 wherein the ultrasonic scanner comprises an ultrasonic transducer and a compression plate having an edge, the ultrasonic transducer disposed at an angle relative to the compression plate so that the ultrasonic transducer provides imaging of regions of the tissue mass located near, or extending beyond, the edge of the compression plate.

11. The apparatus as defined in claim 1 wherein the ultrasonic scanner comprises an ultrasonic transducer and a compression plate having an edge, the ultrasonic transducer and the compression plate disposed at an angle relative to a horizontal plane so that the ultrasonic transducer provides imaging of regions of the tissue mass located near, or extending beyond, the edge of the compression plate.

12. The apparatus as defined in claim 1 wherein the display means displays images of the tissue mass from a selected one of a plurality of orthogonal views.

13. Apparatus for positioning a tip of a biopsy device for insertion into a selected region of a tissue mass, the apparatus for use in a system including display means and an ultrasonic scanner that provides an image of the tissue mass, the apparatus comprising:

a support for holding a tip of a biopsy device with a trajectory;

means, other than the ultrasonic scanners, coupled to the support for generating a signal corresponding to a current location of the tip of the biopsy device, prior to insertion into the tissue mass, the display means displaying the image of the tissue mass including the selected region and a symbol representative of the current location of the tip of the biopsy device relative to the selected region, so that aligning the symbol with the selected region corresponds to moving the support to position at which the trajectory of the tip of the biopsy device will intersect the selected region.

14. The apparatus as defined in claim 13 wherein the support comprises first and second support tracks disposed in orthogonal relation to one another.

15. The apparatus as defined in claim 13 wherein the means for generating a signal comprises at least one encoder.

16. A system including the apparatus as defined in claim 13, wherein the ultrasonic scanner provides real-time imaging of the tissue mass.

17. The system as defined in claim 16 wherein the ultrasonic scanner provides imaging of the tip of the biopsy device after the tip of the biopsy device has been inserted into the tissue mass.

18. The apparatus as defined in claim 13 wherein the support releasably holds the biopsy device, so that the biopsy device may be released from the support after insertion of the tip of the biopsy device into the tissue mass to enable free-hand manipulation of the biopsy device.

19. A system including the apparatus as defined in claim 13, wherein the ultrasonic scanner forms a first compression surface, the system further comprising a tissue support table forming a second compression surface, the tissue mass immobilized between the first and second compression surfaces.

20. The apparatus as defined in claim 14 further comprising a tissue support table, the first support track removably anchored to the tissue support table.

21. The apparatus as defined in claim 14 further comprising a dummy X-ray film cassette, the first support track anchored to the dummy X-ray film cassette.

22. A system including the apparatus as defined in claim 13, wherein the ultrasonic scanner comprises an ultrasonic transducer and a compression plate having an edge, the ultrasonic transducer disposed at an angle relative to the compression plate so that the ultrasonic transducer provides imaging of regions of the tissue mass located near, or extending beyond, the edge of the compression plate.

23. A system including the apparatus as defined in claim 13, wherein the ultrasonic scanner comprises an ultrasonic transducer and a compression plate having an edge, the ultrasonic transducer and the compression plate disposed at an angle relative to a horizontal plane, so that the ultrasonic transducer provides imaging of regions of the tissue mass located near, or extending beyond, the edge of the compression plate.

24. A system including the apparatus as defined in claim 13, wherein the display means displays images of the tissue mass from a selected one of a plurality of orthogonal views.

25. A method of positioning a tip of a biopsy device to have a predetermined trajectory into a selected region of a tissue mass, the method comprising steps of:

immobilizing the tissue mass;

generating an ultrasonic image of the tissue mass including the selected region;

displaying the ultrasonic image of the tissue mass including the selected region;

providing a support for holding a tip of a biopsy device with a trajectory;

generating a signal corresponding to a current location of the tip of the biopsy device, prior to insertion of the tip of the biopsy device into the tissue mass;

displaying a symbol representative of the current location of the tip of the biopsy device relative to the selected region, responsive to the signal; and moving the support to a location at which the symbol is aligned with the selected region, so that the trajectory of the tip of the biopsy device will intersect the selected region.

26. The method as defined in claim 25 further comprising a step of providing a real-time ultrasonic image of the tissue mass.

27. The method as defined in claim 26 further comprising steps of:

inserting the tip of the biopsy device into the tissue mass while providing a real-time ultrasonic image of the tissue mass and the tip of the biopsy device;

displaying the ultrasonic image of the tissue mass and the tip of the biopsy device; and guiding insertion of the tip of the biopsy device into the tissue mass responsive to the displayed image.

28. The method as defined in claim 25 further comprising steps of:

releasing the biopsy device from the support after insertion of the tip of the biopsy device into the tissue mass; and manipulating the biopsy device free-hand to alter the trajectory of the tip of the biopsy device within the tissue mass.

29. The method of claim 25 wherein the step of displaying the ultrasonic image of the tissue mass comprises displaying an elevation view of the tissue mass.

30. The method of claim 27 wherein the step of displaying an ultrasonic image of the tissue mass and the tip of the biopsy device comprises displaying a plan view of the tissue mass and tip of the biopsy device.

* * * * *